United States Patent [19]

Bezwada et al.

[11] Patent Number: 5,076,807

[45] Date of Patent: Dec. 31, 1991

[54] RANDOM COPOLYMERS OF P-DIOXANONE, LACTIDE AND/OR GLYCOLIDE AS COATING POLYMERS FOR SURGICAL FILAMENTS

[75] Inventors: Rao S. Bezwada, Whitehouse Station; Richard L. Kronenthal, Fair Lawn, both of N.J.

[73] Assignee: Ethicon, Inc., Somerville, N.J.

[21] Appl. No.: 388,100

[22] Filed: Jul. 31, 1989

[51] Int. Cl.$^5$ .............................................. A61B 17/00
[52] U.S. Cl. .................................. 606/230; 606/231
[58] Field of Search .......................... 606/230, 231

[56] References Cited

U.S. PATENT DOCUMENTS

| | | |
|---|---|---|
| 3,982,543 | 9/1976 | Schmitt et al. .................... 606/230 |
| 4,052,988 | 10/1977 | Doddi et al. ..................... 606/231 |
| 4,201,216 | 5/1980 | Mattei .............................. 606/230 |
| 4,470,416 | 9/1984 | Kafiawy et al. .................. 606/230 |
| 4,643,191 | 2/1987 | Bezwada et al. ................. 606/230 |
| 4,653,497 | 3/1987 | Bezwada et al. ................. 606/230 |
| 4,705,820 | 11/1987 | Wang et al. ....................... 606/230 |
| 4,838,267 | 6/1989 | Jamiolkowski et al. .......... 606/230 |

Primary Examiner—Stephen C. Pellegrino
Assistant Examiner—Gary Jackson

[57] ABSTRACT

Low molecular weight absorbable copolymers of p-dioxanone with lactide and/or glycolide are used as coatings for surgical filaments to improve tactile smoothness and tie-down properties. These copolymers are prepared by reacting p-dioxanone with lactide and/or glycolide in the presence of an initiator such as a mono- or polyhydric alcohol or a hydroxy acid.

3 Claims, No Drawings

RANDOM COPOLYMERS OF P-DIOXANONE, LACTIDE AND/OR GLYCOLIDE AS COATING POLYMERS FOR SURGICAL FILAMENTS

This invention relates to the synthesis of low molecular weight, random copolymers of p-dioxanone ("PDO") with lactide and/or glycolide, and to the use of these copolymers as absorbable coating polymers for surgical filaments.

BACKGROUND OF THE INVENTION

Surgical filaments such as sutures and ligatures are often coated to improve their tie-down performance and tactile smoothness. Tie-down performance refers to the ease or difficulty of sliding a knot down the filament into place. Tie-down performance is related to tactile smoothness and the tendency of the filament to "grab" or "chatter". Tactile smoothness is also related to the ease with which the filament can be pulled through tissue.

It is customary to coat surgical filaments with materials to improve tie-down and tactile smoothness properties. This invention is directed to the use of a new material for this purpose.

SUMMARY OF INVENTION

Low molecular weight absorbable copolymers of p-dioxanone ("PDO") with lactide and/or glycolide are used as coatings for surgical filaments. These copolymers are prepared by reacting p-dioxanone and lactide and/or glycolide with an initiator such as a mono- or polyhydric alcohol such as diethylene glycol, glycerol, 1-dodecanol, and mannitol, or a hydroxy acid such as lactic or glycolic acid. Molecular weights and viscosities can be controlled by the type of initiator and by the ratio of initiator to monomer. Handling properties of the coating copolymers can be controlled by changing the mole ratios of p-dioxanone, lactide and/or glycolide.

THE PRIOR ART

Schmitt et al., in U.S. Pat. No. 3,982,543, disclose the use of a lactide/glycolode copolymer as a coating for a polyglycolide braided suture (see, especially, Example 10, columns 18-19 of the patent). At Col. 13, line 52, the patentees disclose a terpolymer of PDO (referred to by the patentees as "keto-1,4-dioxane"), lactide, and glycolide. It is not clear from the patent what utility the patentees had in mind for this terpolymer.

Mattei, in U.S. Pat. No. 4,201,216, discloses surgical filaments coated with a mixture of an absorbable, film-forming polymer and a fatty acid salt such as calcium stearate. The film-forming polymer is preferably a copolymer of lactide and glycolide. Broadly, the film-forming polymer can be a hompolymer or copolymer of lactide, glycolide, PDO, and other materials (see col. 3, lines 51 et seq.). The patent teaches that the film-forming polymer without the fatty acid salt is not acceptable as a coating for surgical filaments. E.g., see the Control Example in the table in Column 8.

Bezwada et al., in U.S. Pat. No. 4,643,191, disclose crystalline copolymers of PDO and lactide.

Bezwada et al., in U.S. Pat. No. 4,653,497, disclose crystalline copolymers of PDO and glycolide.

Kafrawy et al., in U.S. Pat. No. 4,470,416, disclose copolymers or lactide and/or glycolide with 1,5-dioxepan-2-one.

Doddi et al, in U.S. Pat. No. 4,052,988, disclose polymers of PDO. Copolymers with other monomers, including lactide and glycolide, are broadly disclosed (see, for example, col. 8, line 64 through col. 9, line 19).

Jamiolkowski et al., in U.S. patent application Ser. No. 155,348, filed on Feb. 12, 1988 and assigned to the same assignee as this application, discloses certain glycolide/PDO block copolymers.

DETAILED DESCRIPTION OF THE INVENTION

The copolymers that are used as coatings in the invention are made by reacting p-dioxanone with lactide and/or glycolide in the presence of an initiator such as a mono-or polyhydric alcohol or a hydroxy acid. The monomers and initiator are usually used in proportions such that the molecular weight of the copolymer is at least about 2000. The initiator is usually used in proportions of from about 0.1 wt % to about 30 wt % (based on weight of monomers). Routine experimentation will suffice to determine the exact ratios that are preferred in individual cases. Type and proportion of initiator control the molecular structure and molecular weight of the copolymer. For instance, a polyhydric alcohol initiator having three or more hydroxy groups will result in a branched chain polymeric structure, whereas a mono- or dihydric alcohol or a hydroxy acid (having ony carboxy group and one hydroxy group) will result in a linear polymeric structure. Also, as a general rule, the molecular weight of the copolymer is inversely proportional to the proportion of hydroxyl equivalents to monomer.

The monomers are used in proportions such that the resulting copolymer is either liquid at room temperature (25° C.) or is a waxy solid at room temperature. As a general rule, the ratio of the monomers used to prepare the copolymer that will meet these requirements is such that from about 0.15 to about 0.5 mole of lactide and/or glycolide is used, the remainder being PDO. The proportion and type of initiator is selected such that the copolymer will have an inherent viscosity of from about 0.05 to about 0.5, and preferably, from about 0.06 to about 0.14, dl/g, determined in hexafluoroisopropyl alcohol at 25° C. and a concentration of 0.1 g/dl. The exact amount and type of initiator required to achieve the desired molecular weight can be determined by routine experimentation, upon reading the disclosure herein, including the extensive experimental section of this specification.

The copolymers are prepared by synthesis techniques that are analogous to processes that are known in the art. For instance, the initiator, monomers, and a suitable esterification or ester exchange catalyst are charged to a suitable vessel and the contents of the vessel are heated to a temperature within the range of from about 80° C. to about 180° C. for a period of from about four hours to about four days. The Examples, below, illustrate typical reaction conditions.

Among the initiators that can be used to prepare the copolymers of the invention are polyalkylene glycols such as diethylene glycol, triethylene glycol, and the like, polyhydroxy alkanes such as ethylene glycol, glycerol, trimethylol propane, pentaerythritol, mannitol, glucose, and the like, and hydroxy acids such as lactic acid and glycolic acid.

Among the esterification or ester exchange catalysts that can be used are stannous octoate, dibutyltin oxide, and the like. The catalyst is usually used in proportions of from about $1 \times 10^{-4}$ to about $1.25 \times 10^{-5}$ mole of catalyst per moles of total initiator and monomer.

The copolymers are used to coat surgical filaments in order to improve the tie-down and tactile smoothness of the filaments. The copolymer can be used as a coating on braided and monofilament sutures and ligatures. The improvements imparted by the copolymers are most pronounced on braided sutures and ligatures. The filaments can be absorbable or non-absorbable. Among the types of filaments which can be coated by the copolymers of the invention are absorbable materials such as polyglycolide, poly(lactide-co-glycolide), poly(p-dioxanone), and other absorbable materials, and non-absorbable materials such as polyester, nylon, silk, polypropylene, and the like.

The copolymers of the invention are coated on the surgical filaments by procedures that are analogous to those that are known in the art. For instance, the filament can be passed through an organic solvent solution of the copolymer, and then passed through a drying oven to evaporate the solvent. As a general rule, coating add-ons of from about 1 to about 10%, based on the weight of the filament, are usually sufficient to achieve the objectives of the invention. The Examples, below, illustrate coating techniques, add-on proportions, and the use of the coatings with various types of filament.

EXAMPLE 1

Preparation of Copolymer of p-dioxanone/L(−)lactide/-glycolide at 50/25/25 Initial Weight Composition A flame dried, 250 milliliter, round bottom, single neck flask was charged with 12.0 milliliters of distilled diethylene glycol ("DEG"), and dried under high vacuum at 40° C. for about 16 hours. Under nitrogen, the reaction flask was charged with 50.0 grams (0.4898 mole) of p-dioxanone, 25.0 grams (0.1735 mole) of L(−) lactide, 25.0 grams (0.2154 mole) of glycolide, and 0.08876 milliliter of stannous octoate ["Sn(Oct)$_2$"−0.33 molar solution in toluene]. The contents of the reaction flask were held under high vacuum at room temperature for about 16 hours. The flask was fitted with a flame dried mechanical stirrer and an adapter with a hose connection. The reactor was purged with nitrogen three times before being vented with nitrogen. The reaction mixture was heated to 180° C. and maintained there for 3 hours. The temperature of the oil bath was lowered to 120° C., and maintained there for 5 hours before dropping the temperature to 80° C., and maintained there for 16 hours. The polymer was dried about 72 hours/80° C./0.1 mm Hg. to remove any unreacted monomer. The resulting copolymer is a viscous liquid, and has an inherent viscosity of 0.10 dl/g. All inherent viscosities "IV's" reported herein were determined at 25° C. at a concentration of 0.1 g/dl in hexafluoroisopropyl alcohol ("HFIP").

EXAMPLE 2

Preparation of Copolymer of p-dioxanone/L(−) lactide at 50/50 Initial Weight Composition This copolymer was prepared under the same conditions described in Example 1 using the following composition:

| p-Dioxanone | 50.0 grams (0.4898 mole) |
| L(-)lactide | 50.0 grams (0.3469 mole) |

| -continued | |
|---|---|
| Diethylene glycol (dist) | 12.0 ml. |
| Sn(Oct)$_2$ (0.33 molar) | 0.0845 ml. |

The resulting copolymer is a viscous liquid, and has an inherent viscosity of 0.092 dl/g.

EXAMPLE 3

Preparation of Copolymer of p-dioxanone/glycolide at 50/50 Initial Weight Composition This copolymer was prepared under the same conditions described in Example 1, with the following composition:

| p-Dioxanone | 50.0 grams (0.4898 mole) |
| Glycolide | 50.0 grams (0.3469 mole) |
| Diethylene glycol (dist.) | 12.0 ml |
| Sn(Oct)$_2$ (0.33 molar) | 0.09299 ml. |

The resulting copolymer is a viscous liquid, and has an inherent viscosity of 0.11 dl/g.

EXAMPLE 4

Copolymer of p-dioxanone/L(−)lactide at 50/50 Initial Weight Composition Using Mannitol as an Initiator This copolymer was prepared under the same conditions described in Example 1, with the following composition:

| p-Dioxanone | 50.0 grams (0.4898 mole) |
| L(-)lactide | 50.0 grams (0.3469 mole) |
| Mannitol | 5.0 grams |
| Sn(Oct)$_2$ (0.33 molar) | 0.0845 ml. |

The resulting copolymer is a viscous liquid, and has an inherent viscosity of 0.14 dl/g.

GPC data of Examples 1–4 are shown in Table I, below. "L" represents lactide, "G" represents glycolide, "PDO" represents p-dioxanone, "DEG" represents diethylene glycol, and "Mw" and "Mn" mean weight average and number average molecular weight, respectively.

TABLE I

| Copolymer | Mw | Mn | % Monomer | Ex. |
|---|---|---|---|---|
| PDO/L/G 50/25/25 by wt. - DEG. | 6200 | 5800 | <1 | 1 |
| PDO/L 50/50 by wt. - DEG. | 6200 | 5800 | <1 | 2 |
| PDO/G 50/50 by wt. - DEG. | 6100 | 5700 | <1 | 3 |
| PDO/L 50/50 by wt. - mannitol | — | — | <1 | 4 |

To lower the viscosity of these copolymers, higher ratios of initiator to monomer (i.e., higher ratio of OH groups in the initiator to monomer) are used. Illustrative examples of this principle are shown below:

EXAMPLE 5

Copolymer of p-dioxanone/L(−)lactide/glycolide at 50/25/25 Initial Weight Composition Using DEG as an Initiator Composition and the heating scheme are shown below:

| Composition | |
|---|---|
| p-Dioxanone | 50.0 grams (0.4898 mole) |
| L(-)lactide | 25.0 grams (0.1735 mole) |
| Glycolide | 25.0 grams (0.2154 mole) |
| DEG (dist) | 15.0 ml |
| Sn(Oct)$_2$ (0.33 M) | 0.0888 ml |
| Heating Scheme | |
| Seven hours at 170° C. | |
| Sixteen hours at 110° C. | |
| Twenty-four hours at 90° C. | |

The copolymer is a viscous liquid, and has an inherent viscosity of 0.097 dl/g.

Final composition was found by NMR to be a polylactic acid/polyglycolic acid/polydioxanone/diesterified (i.e., both hydroxyl groups of the diethylene glycol were esterified) analog of DEG at a ratio of 17.7/18.6/46.9/16.8 by mole.

EXAMPLE 6

Preparation of Copolymer of p-dioxanone/L(-)lactide at 50/50 Initial Weight Composition with Mannitol as an Initiator

| Composition: | |
|---|---|
| p-Dioxanone | 50.0 grams (0.4898 mole) |
| L(-)lactide | 50.0 grams (0.3469 mole) |
| D-Mannitol | 8.0 grams |
| Sn(Oct)$_2$ (0.33 M) | 0.0845 ml. |
| Heating Scheme: | |
| At 160° C./3 hours | |
| 110° C./72 hours | |

The copolymer is a viscous liquid, and has an inherent viscosity of 0.11 dl/g.

EXAMPLE 7

Preparation of Copolymer of p-dioxanone/L(-)lactide at 50/50 Initial Weight Composition with DEG as an Initiator

| Composition: | |
|---|---|
| p-Dioxanone | 50.0 grams (0.4898 mole) |
| L(-)lactide | 50.0 grams (0.3469 mole) |
| DEG (dist.) | 15.0 ml. |
| Sn(Oct)$_2$ (0.33 M) | 0.0845 ml. |
| Heating Scheme: | |
| At 160° C./6 hours | |
| 110° C./16 hours | |
| 90° C./28 hours | |

The copolymer is a viscous liquid, and has an inherent viscosity of 0.08 dl/g. Final composition by NMR found to be polylactic acid/diester analog of DEG/-polydioxanone at proportions of 36.8/16.6/46.5 (polylactic acid/DEG/-polydioxanone) by mole.

EXAMPLE 8

Preparation of Copolymer of p-dioxanone/glycolide at 50/50 Initial Weight Composition with DEG as a Initiator

| Composition: | |
|---|---|
| p-Dioxanone | 50.0 grams (0.4898 mole) |
| Glycolide | 50.0 grams (0.4308 mole) |
| DEG (dist.) | 15.0 ml. |
| Sn(Oct)$_2$ (0.33 M) | 0.0929 ml. |
| Heating Scheme: | |
| At 160° C./7 hours | |
| 110° C./16 hours | |
| 90° C./28 hours | |

The resulting copolymer is a viscous liquid, and has an inherent viscosity of 0.10 dl/g. Final composition by NMR found to be as polylactide acid/diester analog of DEG/polydioxanone at 33.1/16.9/50.0 by mole.

EXAMPLE 9

Preparation of Copolymer of PDO/glycolide at 80/20 initial weight composition with diethylene glycol as an initiator A flame dried, 250 milliliter, round bottom, single neck flask was charged with 12.0 milliliters of distilled diethylene glycol, and dried under high vacuum at 40° C. for about 16 hours. Under nitrogen, the reaction flask was charged with 80.0 grams (0.7836 mole) of p-dioxanone, 20.0 grams (0.1724 mole) of glycolide, and 0.096 milliliter of stannous octoate (0.33 molar solution in toluene). The contents of the reaction flask were held under high vacuum at room temperature for about 16 hours. The flask was fitted with a flame dried mechanical stirrer and an adapter with a hose connection. The reactor was purged with nitrogen three times before being vented with nitrogen. The reaction mixture was heated to 180° C. and maintained there for 3 hours. The temperature of the oil bath was lowered to 120° C., and maintained there for 5 hours. The polymer was dried at 80° C./0.1 mm Hg. to remove any unreacted monomer. The resulting copolymer has an inherent viscosity of 0.12 dl/g.

EXAMPLE 10

Preparation of Copolymer of PDO/glycolide at 80/20 initial weight composition with glycerol as an initiator A flame dried, 250 milliliter, round bottom, single neck flask was charged with 6.0 milliliters of glycerol, and dried under high vacuum at 40° C. for about 16 hours. Under nitrogen, the reaction flask was charged with 80.0 grams (0.7836 mole) of p-dioxanone, 20.0 grams (0.1724 mole) of glycolide, and 0.096 milliliter of stannous octoate (0.33 molar solution in toluene). The contents of the reaction flask were held under high vacuum at room temperature for about 16 hours. The flask was fitted was fitted with a flame dried mechanical stirrer and an adapter with a hose connection. The reactor was purged with nitrogen three times before being vented with nitrogen. The reaction mixture was heated to 180° C. and maintained there for 3 hours. The temperature of the oil bath was lowered to 120° C., and maintained there for 5 hours. The polymer was dried to remove any unreacted monomer. The resulting copolymer has an inherent viscosity of 0.09 dl/g.

EXAMPLE 11

Preparation of Copolymer of PDO/L(-)lactide at 80/20 initial weight composition with diethylene glycol as an initiator A flame dried, 250 milliliter, round bottom, single neck flask was charged with 12.0 milliliters of distilled diethylene glycol, and dried under high vacuum at 40° C. for about 16 hours. Under nitrogen, the reaction flask was charged with 80.0 grams (0.7836 mole) of p-dioxanone, 20.0 grams (0.1388 mole) of L(−) lactide, and 0.093 milliliter of stannous octoate (0.33 molar solution in toluene). The contents of the reaction flask were held under high vacuum at room temperature for about 16 hours. The flask was fitted with a flame dried mechanical stirrer and an adapter with a hose connection. The reactor was purged with nitrogen three times before being vented with nitrogen. The reaction mixture was heated to 170° C. and maintained there for 3 hours. The temperature of the oil bath was lowered to 120° C., and maintained there for 5 hours. The polymer was dried about 96 hours/80° C./0.1 mm to remove any unreacted monomer. The resulting copolymer has an inherent viscosity of 0.11 dl/g.

EXAMPLE 12

Preparation of Copolymer of PDO/L(−)lactide at 80/20 initial weight composition with glycerol as an initiator A flame dried, 250 milliliter, round bottom, single neck flask was charged with 6.0 milliliters of glycerol, and dried under high vacuum at 40° C. for about 16 hours. Under nitrogen, the reaction flask was charged with 80.0 grams (0.7836 mole) of p-dioxanone, 20.0 grams (0.1388 mole) of L(−)lactide, and 0.093 milliliter of stannous octoate (0.33 molar solution in toluene). The contents of the reaction flask were held under high vacuum at room temperature for about 16 hours. The flask was fitted with a flame dried mechanical stirrer and an adapter with a hose connection. The reactor was purged with nitrogen three times before being vented with nitrogen. The reaction mixture was heated to 170° C. and maintained there for 3 hours. The temperature of the oil bath was lowered to 120° C., and maintained there for 5 hours. The polymer was dried about 96 hours/80° C./0.1 mm Hg. to remove any unreacted monomer. The resulting copolymer has an inherent viscosity of 0.14 dl/g.

EXAMPLE 13

Preparation of Copolymer of PDO/L(−)lactide at 80/20 initial weight composition with diethlene glycol as an initiator A flame dried, 250 milliliter, round bottom, single neck flask was charged with 12.0 milliliters of distilled diethylene glycol, and dried under high vacuum at 40° C. for about 16 hours. Under nitrogen, the reaction flask was charged with 80.0 grams (0.7836 mole) of p-dioxanone, 20.0 grams (0.1388 mole) of L(−) lactide, and 0.093 milliliter of stannous octoate (0.33 molar solution in toluene). The contents of the reaction flask were held under high vacuum at room temperature for about 16 hours. The flask was fitted with a flame dried mechanical stirrer and an adapter with a hose connection. The reactor was purged with nitrogen three times before being vented with nitrogen. The reaction mixture was heated to 140° C. and maintained there for 3 hours. The temperature of the oil bath was lowered to 120° C., and maintained there for 5 hours before dropping the temperature to 80° C., and maintained there for 60 hours. The polymer was dried about 72 hours/80° C./0.1 mm Hg. to remove any unreacted monomer. The resulting copolymer has an inherent viscosity of 0.64 dl/g.

EXAMPLE 13

Preparation of Copolymer of PDO/L(−)lactide at 80/20 initial weight composition with diethlene glycol as an initiator A flame dried, 250 milliliter, round bottom, single neck flask was charged with 12.0 milliliters of distilled diethylene glycol, and dried under high vacuum at 40° C. for about 16 hours. Under nitrogen, the reaction flask was charged with 80.0 grams (0.7836 mole) of p-dioxanone, 20.0 grams (0.1388 mole) of L(−) lactide, and 0.093 milliliter of stannous octoate (0.33 molar solution in toluene). The contents of the reaction flask were held under high vacuum at room temperature for about 16 hours. The flask was fitted with a flame dried mechanical stirrer and an adapter with a hose connection. The reactor was purged with nitrogen three times before being vented with nitrogen. The reaction mixture was heated to 140° C. and maintained there for 3 hours. The temperature of the oil bath was lowered to 120° C., and maintained there for 5 hours before dropping the temperature to 80° C., and maintained there for 60 hours. The polymer was dried about 72 hours/80° C./0.1 mm Hg. to remove any unreacted monomer. The resulting copolymer has an inherent viscosity of 0.6 dl/g.

EXAMPLE 14

Preparation of Copolymer of PDO/L(−) lactide at 80/20 initial weight composition with glycerol as an initiator A flame dried, 250 milliliter, round bottom, single neck flask was charged with 6.0 milliliters of glycerol, and dried under high vacuum at 40° C. for about 16 hours. Under nitrogen, the reaction flask was charged with 80.0 grams (0.7836 mole) of p-dioxanone, 20.0 grams (0.1388 mole) of L(−) lactide, and 0.093 milliliter of stannous octoate (0.33 molar solution in toluene). The contents of the reaction flask were held under high vacuum at room temperature for about 16 hours. The flask was fitted with a flame dried mechanical stirrer and an adapter with a hose connection. The reactor was purged with nitrogen three times before being vented with nitrogen. The reaction mixture was heated to 140° C. and maintained there for 3 hours. The temperature of the oil bath was lowered to 120° C., and maintained there for 5 hours before dropping the temperature to 80° C., and maintained there for 60 hours. The polymer was dried about 72 hours/80° C./0.1 mm Hg. to remove any unreacted monomer. The resulting copolymer has an inherent viscosity of 0.11 dl/g.

EXAMPLE 15

Preparation of Copolymer of PDO/L(−) lactide at 70/30 initial weight composition with diethylene glycol as an initiator A flame dried, 250 milliliter, round bottom, single neck flask was charged with 12.0 grams (0.0681 mole) of diethylene glycol, and dried under high vacuum at 40° C. for about 16 hours. Under nitrogen, the reaction flask was charged with 70.0 grams (0.6857 mole) of p-dioxanone, 30.0 grams (0.2081 mole) of L(−) lactide, and 0.090 milliliter of stannous octoate (0.33 molar solution in toluene). The contents of the reaction flask were held under high vacuum at room temperature for about 16 hours. The flask was fitted with a flame dried mechanical stirrer and an adapter with a hose connection.

The reactor was purged with nitrogen three times before being vented with nitrogen. The reaction mixture was heated to 140° C. and maintained there for 3 hours. The temperature of the oil bath was lowered to 120° C., and maintained there for 5 hours before dropping the temperature to 80° C., and maintained there for 60 hours. The polymer was dried about 120 hours/80° C./0.1 mm Hg. to remove any unreacted monomer. The resulting copolymer has an inherent viscosity of 0.10 dl/g.

EXAMPLE 16

Preparation of Copolymer of PDO/glycolide at 70/30 initial weight composition with diethylene glycol as an initiator A flame dried, 250 milliliter, round bottom, single neck flask was charged with 12.0 grams (0.0681/mole) of diethylene glycol, and dried under high vacuum at 40° C. for about 16 hours. Under nitrogen, the reaction flask was charged with 70.0 grams (0.6857 mole) of p-dioxanone, 30.0 grams (0.2585 mole) of glycolide, and 0.095 milliliter of stannous octoate (0.33 molar solution in toluene). The contents of the reaction flask were held under high vacuum at room temperature for about 16 hours. The flask was fitted with a flame dried mechanical stirrer and an adapter with a hose connection. The reactor was purged with nitrogen three times before being vented with nitrogen. The reaction mixture was heated to 140° C. and maintained there for 3 hours. The temperature of the oil bath was lowered to 120° C., and maintained there for 5 hours before dropping the temperature to 80° C., and maintained there for 60 hours. The polymer was dried about 120 hours/80° C./0.1 mm Hg. to remove any unreacted monomer. The resulting copolymer has an inherent viscosity of 0.09 dl/g.

EXAMPLE 17

Preparation of copolymer of p-dioxanone/glycolide at 50/50 initial weight composition with glycolic acid as an initiator

| Composition: | |
|---|---|
| p-Dioxanone | 50.0 grams (0.4898 mole) |
| glycolide | 50.0 grams (0.4308 mole) |
| glycolic acid | 10.10 grams |
| Sn(Oct)$_2$ (0.33 M) | 0.0929 ml |
| Heating Scheme: | |
| At 160° C./7 hours | |
| 110° C./16 hours | |
| 90° C./24 hours | |

The resulting copolymer is a viscous liquid, and has an inherent viscosity of 0.13 dl/g. after devolatilization.

EXAMPLE 18

Preparation of copolymer of p-dioxanone/glycolide at 50/50 initial weight composition with 20 parts of glycolic acid as an initiator

| Composition: | |
|---|---|
| p-Dioxanone | 50.0 grams (0.4898 mole) |
| glycolide | 50.0 grams (0.4308 mole) |
| glycolic acid | 20.0 grams |
| Sn(Oct)$_2$ (0.33 M) 0.0929 | ml |
| Heating Scheme: | |
| At 160° C./7 hours | |
| 110° C./16 hours | |
| 90° C./24 hours | |

The resulting copolymer is a viscous liquid, and has an inherent viscosity of 0.093 dl/g, after devolatilization.

EXAMPLE 19

Preparation of copolymer of p-dioxanone/glycolide/glycolic acid at 50/25/25 initial weight composition

| Composition: | |
|---|---|
| p-dioxanone | 50.0 grams |
| glycolide | 25.0 grams |
| glycolic acid | 25.0 grams |
| Sn(Oct)$_2$ (0.33 M) | 0.0929 ml |
| Heating Scheme: | |
| At 160° C./7 hours | |
| 110° C./16 hours | |
| 90° C./24 hours | |

The resulting copolymer is a viscous liquid, and has an inherent viscosity of 0.11 dl/g, after devolatilization.

EXAMPLE 20

Preparation of copolymer of p-dioxanone/L(−)lactide at 50/50 initial weight composition using 20% glycolic acid as an initiator

| Composition: | |
|---|---|
| p-dioxanone | 50.0 g (0.4898 mole) |
| L(-) lactide | 50.0 g (0.3469 mole) |
| glycolic acid | 20.0 g |
| Sn(Oct)$_2$ (0.33 M) | 0.0845 ml |
| Heating Scheme: | |
| At 160° C./7 hours | |
| 110° C./16 hours | |
| 90° C./24 hours | |

The resulting copolymer is a viscous liquid and has an inherent viscosity of 0.08 dl/g.

These copolymers were applied to uncoated poly(-lactide-co-glycolide) sutures at 3% and 5% solutions in 1,1,2-trichloroethane. The concentration of the copolymers in solvent may range from 1 to 10% by wt. based on the solvent. The sutures (each about 18 inches long) were immersed in coating solutions (each solution had a volume of about 100 ml), air dried at room temperature for 15-30 minutes, and then dried under vacuum for about 16 hours at room temperature. The suture size, percent coating material in solvent, and percent coating on suture (add-on) are listed in Tables II to V, below.

The sutures were immersed in the coating solution of 1,1,2-trichloroethane for about 1-2 mins. air dried for about 30 minutes at room temperature, and then dried under vacuum at room temperature for about 16 hours. The percentage coating on suture was calculated by weighing the suture before and after coating, and the data is given in Tables II to V. After drying, the coated sutures were stored in a nitrogen box.

TABLE II

| Example | Suture Size | % Coating Material in Solvent | % Coating On Suture |
| --- | --- | --- | --- |
| 1 | 4-0 | 3 | 2.27 |
| 2 | 4-0 | 3 | 1.43 |
| 3 | 4-0 | 3 | 1.65 |
| 4 | 4-0 | 3 | 1.65 |
| 5 | 4-0 | 3 | 1.30 |
| 6 | 4-0 | 3 | 1.65 |
| 7 | 4-0 | 3 | 2.32 |
| 8 | 4-0 | 3 | 1.87 |
| 9 | 4-0 | 3 | 1.37 |
| 10 | 4-0 | 3 | 1.41 |
| 11 | 4-0 | 3 | 1.61 |
| 12 | 4-0 | 3 | 1.26 |
| 13 | 4-0 | 3 | 1.62 |
| 14 | 4-0 | 3 | 1.50 |
| 15 | 4-0 | 3 | 2.12 |
| 16 | 4-0 | 3 | 0.81 |
| 17 | 4-0 | 3 | 1.27 |
| 18 | 4-0 | 3 | 1.61 |
| 19 | 4-0 | 3 | 2.51 |
| 20 | 4-0 | 3 | 1.60 |

TABLE III

| Example | Suture Size | % Coating Material in Solvent | % Coating On Suture |
| --- | --- | --- | --- |
| 1 | 4-0 | 5 | 2.61 |
| 2 | 4-0 | 5 | 2.42 |
| 3 | 4-0 | 5 | 2.44 |
| 4 | 4-0 | 5 | 2.30 |
| 5 | 4-0 | 5 | 2.19 |
| 6 | 4-0 | 5 | 2.33 |
| 7 | 4-0 | 5 | 3.54 |
| 8 | 4-0 | 5 | 2.79 |
| 9 | 4-0 | 5 | 2.26 |
| 10 | 4-0 | 5 | 2.27 |
| 11 | 4-0 | 5 | 2.50 |
| 12 | 4-0 | 5 | 2.60 |
| 13 | 4-0 | 5 | 2.02 |
| 14 | 4-0 | 5 | 2.14 |
| 15 | 4-0 | 5 | 2.03 |
| 16 | 4-0 | 5 | 2.50 |
| 17 | 4-0 | 5 | 1.75 |
| 18 | 4-0 | 5 | 2.53 |
| 19 | 4-0 | 5 | 2.40 |
| 20 | 4-0 | 5 | 2.29 |

TABLE IV

| Example | Suture Size | % Coating Material in Solvent | % Coating On Suture |
| --- | --- | --- | --- |
| 1 | 0 | 3 | 1.43 |
| 2 | 0 | 3 | 1.18 |
| 3 | 0 | 3 | 1.00 |
| 4 | 0 | 3 | 1.01 |
| 5 | 0 | 3 | 1.24 |
| 6 | 0 | 3 | 1.10 |
| 7 | 0 | 3 | 1.21 |
| 8 | 0 | 3 | 1.24 |
| 9 | 0 | 3 | 1.25 |
| 10 | 0 | 3 | 1.14 |
| 11 | 0 | 3 | 1.21 |
| 12 | 0 | 3 | 1.53 |
| 13 | 0 | 3 | 1.24 |
| 14 | 0 | 3 | 1.28 |
| 15 | 0 | 3 | 1.35 |
| 16 | 0 | 3 | 1.21 |
| 17 | 0 | 3 | 1.19 |
| 18 | 0 | 3 | 1.25 |
| 19 | 0 | 3 | 1.32 |
| 20 | 0 | 3 | 1.01 |

TABLE V

| Example | Suture Size | % Coating Material in Solvent | % Coating On Suture |
| --- | --- | --- | --- |
| 1 | 0 | 5 | 2.10 |
| 2 | 0 | 5 | 1.84 |
| 3 | 0 | 5 | 2.10 |
| 4 | 0 | 5 | 1.96 |
| 5 | 0 | 5 | 1.78 |
| 6 | 0 | 5 | 1.76 |
| 7 | 0 | 5 | 2.13 |
| 8 | 0 | 5 | 2.07 |
| 9 | 0 | 5 | 2.05 |
| 10 | 0 | 5 | 1.97 |
| 11 | 0 | 5 | 2.21 |
| 12 | 0 | 5 | 1.70 |
| 13 | 0 | 5 | 2.07 |
| 14 | 0 | 5 | 1.88 |
| 15 | 0 | 5 | 1.75 |
| 16 | 0 | 5 | 1.69 |
| 17 | 0 | 5 | 1.75 |
| 18 | 0 | 5 | 1.69 |
| 19 | 0 | 5 | 1.79 |
| 20 | 0 | 5 | 1.75 |

Uncoated and coated sutures were examined for flexibility, smoothness, and subjective tie-down. The tie-down properties of these sutures were determined by tying tightly a two throw square knot and then holding at the ends of the suture and pulling apart. The handling properties of these sutures are compared with uncoated control filaments and with commercial coated poly(lactide-co-glycolide) ("PGA-1") and polyglycolide ("PGA-2") sutures in Tables VI and VII.

TABLE VI

| Handling Properties | Control | Size 4/0 Coated With 3% Solution | Size 4/0 Coated With 5% Solution | Commercial PGA's PGA-1 | Commercial PGA's PGA-2 |
| --- | --- | --- | --- | --- | --- |
| Tactile Smoothness | Smooth | Smooth | Smooth | Smooth | Smooth |
| Subjective Tie Down (dry) | Severe slip-stick action. Graspy feeling while tyeing down | Slipstick action but better than control | Smooth Better than control & 3% solution | Smooth | Severe slipstick action |

TABLE VII

| Handling Properties | Control | Size - 0 Coated With 3% Solution | Size - 0 Coated With 5% Solution | Commercial PGA's PGA-1 | Commercial PGA's PGA-2 |
| --- | --- | --- | --- | --- | --- |
| Tactile Smoothness | Smooth | Smooth | Smoother | Smooth | Smooth |
| Subjective | Smooth, but | Smooth, but | Smooth | Smooth | Smooth |

TABLE VII-continued

| Handling Properties | Control | Size - 0 Coated With | | Commercial PGA's | |
| --- | --- | --- | --- | --- | --- |
| | | 3% Solution | 5% Solution | PGA-1 | PGA-2 |
| Tie-down (dry) | roughness can be felt while tying down (graspy) | roughness can be felt while tying down (graspy) | | | |

The tie-down properties of uncoated PGA sutures are improved when coated with 5% solutions of random copolymers of p-dioxanone and lactide and/or glycolide at various mole ratios and molecular weights. At higher concentrations of the coating solutions, the tie-down properties and smoothness of the braided suture can be improved further. Tactile smoothness and subjective tie-down (dry) of PGA sutures with 5% solution of random copolymers of p-dioxanone and lactide and/or glycolide are equivalent to or better than commercial coated poly(lactide-co-glycolide) and polyglycolide sutures.

The tie-down smoothness test is carried out by a panel of operators who assess the smoothness of a suture during tie-down by snugging down a one-throw knot. The term "slipstick" refers to a phenomenom wherein the suture does not snug down in one smooth stroke, e.g., if a suture "chatters" or has a graspy feeling during tie-down, it is said to have slipstick.

What is claimed is:

1. A surgical filament having improved tie-down properties characterized in that the surface of the filament is coated with a random copolymer of p-dioxanone and at least one of lactide and glycolide wherein:
    said random copolymer is prepared by polymerizing, in the presence of an esterification or ester exchange catalyst, a mixture of (a) an initiator comprising a mono- or polyhydric alcohol or a hydroxy acid and (b) a monomer mixture comprising (i) lactide, glycolide, or mixture thereof, and (ii) p-dioxanone, in the molar proportion of from about 0.15 to about 0.5 mole of lactide, glycolide, or mixture thereof, the remainder being p-dioxanone, wherein the initiator is employed in the proportion of from about 0.1 wt % to about 30 wt %, based on weight of said monomer mixture; and
    said random copolymer has an inherent viscosity of from about 0.05 to about 0.5 dl/g, tested at 25° C. in hexafluoroisopropyl alcohol at a concentration of 0.1 gram of polymer per deciliter of solution.

2. The surgical filament of claim 1 wherein said copolymer has an inherent viscosity of from about 0.06 to about 0.14 dl/g.

3. The surgical filament of claim 1 wherein the initiator is selected from the group consisting of diethylene glycol, mannitol, glycerol, and glycolic acid.

* * * * *